United States Patent [19]

Boesenberg et al.

[11] Patent Number: 4,814,459
[45] Date of Patent: Mar. 21, 1989

[54] BENZOXAZOLYL- AND BENZOTHIAZOLYL-AMINO ACIDS, THEIR PREPARATION AND THEIR USE IN PLANT PROTECTION

[75] Inventors: Heinz Boesenberg, Hofheim am Taunus; Hilmar Mildenberger, Kelkheim; Klaus Bauer, Rodgau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 738,602

[22] Filed: May 28, 1985

[30] Foreign Application Priority Data

May 29, 1984 [DE] Fed. Rep. of Germany ....... 3419994

[51] Int. Cl.$^4$ .................. C07D 277/72; C07D 277/68; C07D 275/06
[52] U.S. Cl. ........................................ 548/161; 71/90
[58] Field of Search ................... 71/90; 548/161, 212, 548/163

[56] References Cited

U.S. PATENT DOCUMENTS

| 2,833,689 | 5/1958 | Gerjovich | 548/163 |
| 3,530,148 | 9/1970 | Nair et al. | 548/161 |
| 4,148,798 | 4/1979 | Wade et al. | 548/212 |
| 4,476,137 | 10/1984 | Haviv et al. | 548/161 |
| 4,554,355 | 11/1985 | Musser | 548/161 |

OTHER PUBLICATIONS

Helvetica Chimica Acta 50 (1967), pp. 1084–1086; Suter et al, "Studien Über, etc.".
Journal of Pharmaceutical Sciences, 57 (1968), pp. 1693–1696, No. 10, Advani et al, "Potential Antineoplastic, etc.".

Primary Examiner—Catherine L. Mills
Attorney, Agent, or Firm—Curtis, Morris & Safford

[57] ABSTRACT

Compounds of the formula

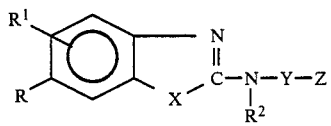

in which X denotes O or S; R and $R^1$ denote H, halogen, alkyl, alkoxy, CN, $NO_2$ or $CF_3$; $R^2$ denotes H or alkyl; Y denotes an optionally substituted alkylene or phenylene group and Z denotes a carboxyl, carboxylate, carboxylic acid ester, carboxamide, nitrile or thioamide group, are suitable for reducing the phytotoxicity of herbicides in useful plants.

8 Claims, No Drawings

BENZOXAZOLYL- AND BENZOTHIAZOLYL-AMINO ACIDS, THEIR PREPARATION AND THEIR USE IN PLANT PROTECTION

The present invention relates to plant-protecting agents which contain compounds of the general formula

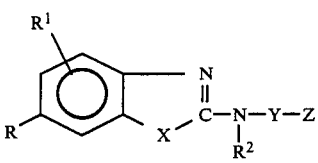
(I)

in which X denotes O or S; R and $R^1$ denote hydrogen, halogen, $(C_1-C_4)$-alkyl, $(C_1-C_4)$-alkoxy, CN, $NO_2$ or $CF_3$; $R^2$ denotes hydrogen or $(C_1-C_4)$-alkyl; Y denotes straight-chain or branched $(C_1-C_8)$-alkylene, 1-3 carbon atoms of which are in a straight chain between the amine nitrogen and the group Z; or denotes methylthio-$(C_1-C_3)$-alkylene, phenyl-$(C_1-C_3)$-alkylene or phenylene; Z denotes

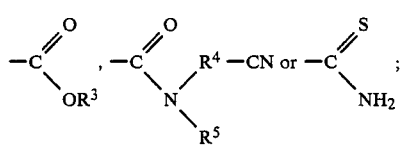

$R^3$ denotes H, $(C_1-C_8)$-alkyl, which can optionally be substituted by halogen or $(C_1-C_2)$-alkoxy, or is $(C_3-C_4)$-alkenyl, $(C_3-C_4)$-alkynyl or the cation of an inorganic or organic base; $R^4$ denotes H or $(C_1-C_6)$-alkyl; $R^5$ denotes H, $(C_1-C_6)$-alkyl or phenyl, which can optionally be mono- or di-substituted by halogen, $(C_1-C_4)$-alkyl or $(C_1-C_4)$-alkoxy; or $R^4$ and $R^5$ together with the nitrogen atom denote a pyrrolidino, piperidino or morpholino radical.

Examples of possible cations are the following:

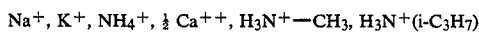

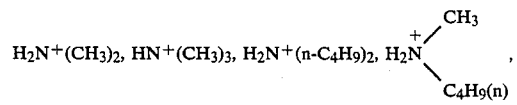

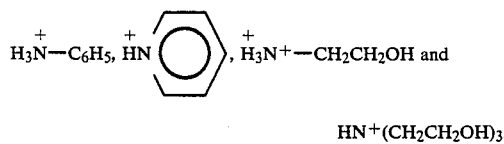

$HN^+(CH_2CH_2OH)_3$.

Preferred plant-protecting agents are those compounds of the formula I in which the benzoxazolyl or benzothiazolyl radical is unsubstituted or monosubstituted by halogen in the aromatic ring, $R^2$ denotes H or methyl, Y denotes $C_1$- or $C_2$-alkylene, Z denotes the group $-COOR^3$ and $R^3$ denotes $(C_1-C_8)$-alkyl, $(C_3-C_4)$-alkenyl, $(C_3-C_4)$-alkynyl or a cation.

Some compounds of the general formula I—without exception those where $R=R^1=R^2=H$—are described in the literature [Helv. Chim. Acta 50 (1967), 1084–86; and J. Pharm. Sc. 57 (1968), 1693–96]. These substances have been synthesized in connection with pharmaceutical problems and have proved to be inactive in this sector. The other compounds of the formula I, however, are novel.

The invention thus also relates to the compounds of the formula I as such, with the exception of those in which R, $R^1$ and $R^2$ simultaneously denote hydrogen, and to processes for their preparation.

The novel compounds are obtained by (a) reacting compounds of the formula

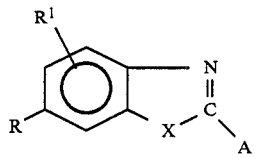
(II)

in which A denotes a group which can easily be split off ("leaving group"), with compounds of the formula

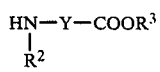
(III)

or (b) reacting compounds of the formula

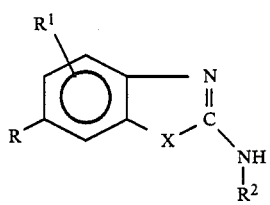
(IV)

with compounds of the formula

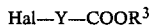
(V)

and, if desired, converting the resulting compounds into other compounds of the formula I in a manner which is known per se, for example by esterification, hydrolysis, salt formation, amidation, alkylation or dehydration. R, $R^1$, $R^2$, $R^3$, X and Y in the formulae II-V have the meaning given, but with the proviso that at least one of the radicals R, $R^1$ and $R^2$ is other than hydrogen.

Re (a) The compounds of the formula III can be employed in the form of the free amino acids, the amino acid esters or their hydrohalides, preferably the hydrochlorides. The chlorine or bromine compounds are preferably used as compounds of the formula II, and in this case the reaction is carried out at temperatures between 20° and 150° C., preferably at 50° to 120° C., with the addition of agents which bond hydrogen halide. Suitable solvents are alcohols, such as methanol, ethanol, isopropanol and n-butanol; ethers, such as diethyl ether, diisopropyl ether, di-n-butyl ether, ethylene glycol dimethyl ether, tetrahydrofuran or 1,4-dioxane; esters, such as ethyl acetate or n-butyl acetate; hydrocarbons, such as hexane, benzene, toluene or xylene; and halogenohydrocarbons, such as methylene chloride, chloroform, 1,2-dichloroethane or chlorobenzene. Polar solvents, such as water, acetonitrile, dimethylformamide, dimethylsulfoxide and N-methylpyrrolidone, or mixtures of the above-mentioned solvents can also be employed.

Suitable agents which bond hydrogen halide are NaOH, KOH, NaHCO$_3$ and K$_2$CO$_3$, and furthermore tertiary amines, such as triethylamine, pyridine, N,N-dimethylaniline or an excess of the amino acid employed or the ester thereof.

Instead of the halogen derivatives II, it is also possible to use starting substances with other groups in the 2-position which can easily be split off ("leaving groups"). Groups which are suitable for this reaction are, for example, alkylthio, alkylsulfinyl or alkylsulfonyl groups, such as the methylthio, ethylsulfinyl or methylsulfonyl radical. Aromatic leaving groups, such as the 4-toluene-sulfonyl group, can also be used. The reaction here is carried out at somewhat higher temperatures or between 50° and 200° C.—preferably at 80° to 150° C.—and in the presence of an inert, higher-boiling solvent, such as toluene, xylene or chlorobenzene.

Re (b): The reverse reaction of 2-amino-benzoxazoles or -benzothiazoles IV with α-halogeno-carboxylic acids or esters thereof proceeds under the same conditions as described under (a).

The resulting compounds of the formula I can be converted into other derivatives of the formula I in a known manner. Thus, the free acids or their salts are obtained by hydrolysis of the esters. The amides are obtained by aminolysis of the esters or by reaction of the free acids by the carbonyl-diimidazolide method. Other esters are formed by esterification of the free acids. Dehydration of amides gives the nitriles (Z=CN), which can in turn be converted into thioamides (Z=—CSNH$_2$) with H$_2$S. Finally, the compounds where R$^2$=H can be alkylated, if desired, on the nitrogen. All of these reactions are well-known to the expert and require no further explanation.

Surprisingly, it has been found that the compounds of the formula I have the properties of reducing and eliminating phytotoxic side effects of plant protection agents, in particular of herbicides, when used in crops of useful plants.

The agents according to the invention can thus be applied before, after or (preferably) at the same time as other herbicides and are then capable of antagonizing, i.e. eliminating, any harmful side effects these herbicides may have on useful plants, without impairing their desirable herbicidal activity. The field of use of conventional plant protection agents can thereby be substantially increased. Such compounds which have the properties mentioned are called "antidotes" or "safeners".

The use of safeners for protecting crops of useful plants from damage by herbicides has been known per se for a relatively long time. However, benzoxazol-2-yl- or benzothiazol-2-yl-amino acids and their derivatives of the general formula I have not hitherto been used as safeners.

Herbicides of which the phytotoxic side effects can be reduced by means of compounds of the formula I are, for example, substituted phenoxyphenoxy-carboxylic acid esters and benzoxazolyloxy-, benzothiazolyloxy- and benzylphenoxy-carboxylic acid esters, and furthermore dimedone oxime derivatives. The following herbicides may be mentioned as examples, without a limitation thereby being imposed:

Phenoxycarboxylic esters, such as methyl 2-(4-(2,4-dichlorophenoxy)-phenoxy)-propionate diclofop-methyl), methyl 2-(4-(4-bromo-2-chlorophenoxy)-phenoxy)-propionate, methyl 2-(4-trifluoromethyl-phenoxy)-phenoxy-propionate, methyl 2-(4-(2-chloro-4-trifluoromethylphenoxy)-phenoxy)-propionate, methyl 2-(4-(2,4-dichlorobenzyl-phenoxy)-propionate, ethyl 2-(4-(4-trifluoromethylphenoxy)-phenoxy)-2-pentene-1-carboxylate, ethyl 2-(4-(6-chlorobenzoxazol-2-yl-oxy)-phenoxy)-propionate (fenoxaprop-ethyl) and ethyl 2-(4-(6-chlorobenzothiazol-2-yl-oxy)-phenoxy)-propionate, and dimedone derivatives, such as 2-(N-ethoxybutyrimidoyl)-5-(2-ethylthiopropyl)-3-hydroxy-2-cyclohexen-1-one or 2-(1-allyloxyiminobutyl)-4-methoxycarbonyl-5,5-dimethyl-3-oxocyclohexenol.

For application, the compounds of the formula I can be formulated with the customary formulation auxiliaries to give dusts, wettable powders, dispersions, emulsion concentrates and the like which contain the active substance in concentrations of 2–80% and are either used as such (dusts, pellets) or dissolved in a solvent (water) or dispersed before use.

The ratio of antidote:herbicide can vary within wide limits between 0.01 and 10 parts of antidote per part of herbicide. The particular optimum amounts of herbicide and antidote depend on the type of herbicide or antidote used and on the type of the plant crop to be treated, and can be determined from case to case by appropriate experiments.

The main fields of use for the agents according to the invention are, above all, crops of cereals (wheat, rye, barley and oats), rice, maize and millet.

Depending on the properties, the agents according to the invention can be used for pretreating the seed of the crop plant (seed dressing), or in the seed furrows before sowing, or as a tank mix before or after emergence of the plants. Pre-emergence treatment includes both the treatment of the area under cultivation before sowing and treatment of the sown cultivation areas on which there is not yet growth.

In principle, the antidote can be applied before, after or at the same time as a herbicide, but simultaneous application in the form of tank mixes or, if appropriate, finished formulations is preferred.

The halogeno-benzoxaoles and halogeno-benzothiazoles required as starting substances for the synthesis can be prepared by methods which are known from the literature [J. prakt. Chem. [2], 42, 454; J. org. Chem. 23 (1958), 1500, 1502; German Pat. No. A-516,998; and J. Ind. Chem. Soc. 10 (1933), 563, 569].

Numerous preparation routes are likewise described in the literature for the amino acids required and their derivatives [compare Houben-Weyl, Method. der org. Chem. (Methods of Organic Chemistry), Volume XI/2 (1958), 269–511].

EXAMPLE 1

N-Methyl-N-[6-chloro-benzothiazol-2-yl]-glycine

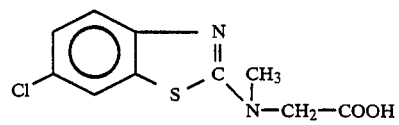

600 ml of absolute dimethyl sulfoxide were intitially introduced into a 1 liter four-necked flask with a thermometer, condenser with a CaCl$_2$ drying tube and gas inlet tube. A gentle stream of dry nitrogen was passed over the surface of the liquid and 66 g (1.65 moles) of NaOH (powdered) were rapidly introduced, with stirring, followed by 73.5 g (0.825 mole) of N-methyl-glycine (sarcosine), in small portions. The sodium salt of the sarcosine is formed, with gentle warming. The mixture was subsequently stirred at 25°–30° C. for 30 minutes and 153 g (0.75 mole) of 2,6-dichlorobenzothiazole were then added in portions at a rate such that the temperature of the highly exothermic reaction did not rise above 75°–80° C. The mixture was then stirred at 95°–100° C. for 5 hours, cooled, poured into about 2 liters of ice-water and acidified (pH 2–3). The chlorobenzothiazolyl-sarcosine which precipitated was filtered off with suction, washed with cold water until free from acid and dried over CaCl$_2$ in vacuo at 50°–60° C. Yield: 171 g (88.8% of theory), melting point: 161°–163° C.

EXAMPLE 2

N-Methyl-N-[6-chloro-benzothiazol-2-yl]-glycine ethyl ester

The ethyl ester of the amino acid prepared in Example 1 was obtained by heating the free acid (145 g=0.565 mole) in 1,100 ml of absolute ethanol, with the addition of 50 g of concentrated sulfuric acid, for 10 hours and then distilling off most of the excess alcohol and pouring the concentrated solution into ice-cold aqueous NaHCO$_3$ solution. The crude ester (151 g) was recrystallized from ethanol. Yield: 114 g (70.9% of theory), melting point: 97°–99° C.

EXAMPLE 3

N-[Benzoxazol-2-yl]glycine ethyl ester

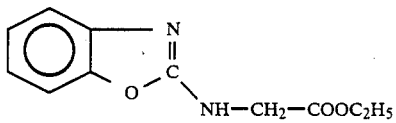

22.3 g (0.16 mole) of glycine ethyl ester hydrochloride were stirred in small portions into a mixture of 23.0 g (0.15 mole) of 2-chlorobenzoxazole, 250 ml of absolute acetonitrile and 44.2 g (0.32 mole) of anhydrous K$_2$CO$_3$ at 50° C. in the course of 3 hours, with stirring. The mixture was subsequently stirred under gentle reflux (80°–82° C.) for a further 4 hours, cooled in an ice-water bath and poured into about 750 ml of ice-water.

The reaction product which precipitated was filtered off with suction, washed with water and a little ice-cold ethanol and dried in vacuo over CaCl$_2$. Yield: 26.0 g (78.8% of theory), melting point: 102°–104° C.

The following compounds are obtained in an analogous manner.

TABLE 1

Benzoxazol-2-yl- and benzothiazol-2-yl-amino acids and derivatives

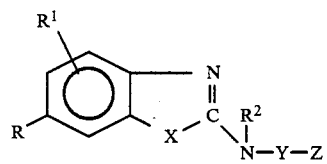

| Example No. | R | R$^1$ | R$^2$ | X | Y | Z | Melting point [°C.] |
|---|---|---|---|---|---|---|---|
| 4 | H | H | H | O | —CH$_2$— | —C(=O)OH | 193–196 |
| 5 | H | 5-CH$_3$ | H | O | —CH$_2$— | —C(=O)OC$_2$H$_5$ | 96–98 |
| 6 | H | 5-CH$_3$ | —CH$_3$ | O | —CH$_2$— | —C(=O)OC$_2$H$_5$ | 60–63 |
| 7 | Cl | H | H | O | —CH$_2$— | —C(=O)OC$_2$H$_5$ | 128–130 |
| 8 | Cl | H | H | O | —CH(CH$_3$)— | —C(=O)OC$_2$H$_5$ | 68 |
| 9 | H | H | —CH$_3$ | O | —CH$_2$— | —C(=O)OC$_2$H$_5$ | 68–70 |

TABLE 1-continued

Benzoxazol-2-yl- and benzothiazol-2-yl-amino acids and derivatives

| Example No. | R | R¹ | R² | X | Y | Z | Melting point [°C.] |
|---|---|---|---|---|---|---|---|
| 10 | Cl | H | —CH₃ | O | —CH₂— | —C(=O)OH | 183–185 |
| 11 | Cl | H | —CH₃ | O | —CH₂— | —C(=O)OCH₃ | 102–104 |
| 12 | Cl | H | —CH₃ | O | —CH₂— | —C(=O)OC₂H₅ | 85–87 |
| 13 | Cl | H | —CH₃ | O | —CH₂— | —C(=O)OC₃H₇(i) | 98–100 |
| 14 | Cl | H | —CH₃ | O | —CH₂— | —C(=O)O—C₆H₁₃(n) | 64–66 |
| 15 | Cl | H | —CH₃ | O | —CH₂— | —C(=O)O—CH₂—CH₂Cl | 73–75 |
| 16 | Cl | H | —CH₃ | O | —CH₂— | —C(=O)NH—C₃H₇—(i) | 203–205 |
| 17 | Cl | H | —CH₃ | O | —CH₂—CH₂— | —CN | 96–98 |
| 18 | H | H | H | O | —CH₂—CH₂—CH₂— | —C(=O)OC₂H₅ | 70–72 |
| 19 | Cl | H | H | O | —HC(CH₂—CH₂—SCH₃)— | —C(=O)OH | 144–146 |
| 20 | Cl | H | H | O | —C₆H₄— (para) | —C(=O)OC₂H₅ | 225–230 |
| 21 | H | H | H | O | —CH₂— | —C(=O)OCH₃ | 98 |
| 22 | H | H | —CH₃ | O | —CH₂— | —C(=O)OC₃H₇(i) | 92 |

TABLE 1-continued

Benzoxazol-2-yl- and benzothiazol-2-yl-amino acids and derivatives $$\text{R}-\underset{\text{R}^1}{\text{[benzene ring]}}-\underset{X}{\overset{N}{\|}}\text{C}-\underset{\underset{N-Y-Z}{|}}{\overset{R^2}{\text{C}}}$$

| Example No. | R  | R¹ | R²   | X | Y              | Z                                              | Melting point [°C.] |
|-------------|----|----|------|---|----------------|------------------------------------------------|---------------------|
| 23          | H  | H  | —CH₃ | O | —CH₂—          | —C(=O)O⁻ Na⁺                                   |                     |
| 24          | Cl | H  | —CH₃ | O | —CH₂—          | —C(=O)O⁻ Na⁺                                   |                     |
| 25          | Cl | H  | —CH₃ | O | —CH₂—          | —C(=O)O⁻ H₃N⁺—C₃H₇(i)                          |                     |
| 26          | H  | H  | H    | S | —CH₂—          | —C(=O)OC₂H₅                                    | 82–83               |
| 27          | H  | H  | H    | S | —CH(CH₃)—      | —C(=O)OC₂H₅                                    | 63–65               |
| 28          | H  | H  | H    | S | —CH₂—CH₂—      | —C(=O)OH                                       | 200–203             |
| 29          | H  | H  | H    | S | —CH₂—CH₂—      | —C(=O)OCH₃                                     | 91–94               |
| 30          | H  | H  | H    | S | —CH₂—CH₂—      | —C(=O)OC₂H₅                                    | 87–88               |
| 31          | H  | H  | H    | S | —CH₂—CH₂—CH₂—  | —C(=O)OH                                       | 132–134             |
| 32          | H  | H  | H    | S | —CH₂—CH₂—CH₂—  | —C(=O)OC₂H₅                                    | 65–66               |
| 33          | Cl | H  | H    | S | —CH₂—          | —C(=O)OC₂H₅                                    | 144–146             |
| 34          | Cl | H  | H    | S | —CH(CH₃)—      | —C(=O)OC₂H₅                                    | 111–113             |

TABLE 1-continued

Benzoxazol-2-yl- and benzothiazol-2-yl-amino acids and derivatives

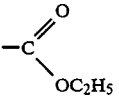

| Example No. | R | R¹ | R² | X | Y | Z | Melting point [°C.] |
|---|---|---|---|---|---|---|---|
| 35 | Cl | H | H | S | —CH₂—CH₂— | —C(=O)OC₂H₅ | 110–112 |
| 36 | Cl | H | H | S | —CH₂—CH₂— | —C(=O)O—C₃H₇(i) | 115–117 |
| 37 | Cl | H | H | S | —CH(C₂H₅)— | —C(=O)OC₂H₅ | 105–107 |
| 38 | Cl | H | H | S | —CH₂—CH₂—CH₂— | —C(=O)OH | 178–179 |
| 39 | Cl | H | H | S | —CH₂—CH₂—CH₂— | —C(=O)OC₂H₅ | 120–121 |
| 40 | Cl | H | H | S | —CH(CH₂—CH₂—SCH₃)— | —C(=O)OH | 159–162 |
| 41 | Cl | H | H | S | —CH(CH₂—CH₂—SCH₃)— | —C(=O)OCH₃ | 79–83 |
| 42 | Cl | H | H | S | —CH(CH₂—CH₂—SCH₃)— | —C(=O)OC₂H₅ | 80–82 |
| 43 | Cl | H | H | S | —CH(CH₂—CH₂—SCH₃)— | —C(=O)O—C₃H₇(i) | 91–92 |
| 44 | Cl | H | H | S | —CH(C₆H₅)— | —C(=O)OH | 231–35 (decomposition) |
| 45 | Cl | H | H | S | —CH(C₆H₅)— | —C(=O)OC₂H₅ | 134–138 |

TABLE 1-continued

Benzoxazol-2-yl- and benzothiazol-2-yl-amino acids and derivatives

| Example No. | R | R¹ | R² | X | Y | Z | Melting point [°C.] |
|---|---|---|---|---|---|---|---|
| 46 | Cl | H | H | S | −CH(C₆H₅)− | −C(=O)OCH₃ | 179–182 |
| 47 | Cl | H | H | S | −CH(CH₂C₆H₅)− | −C(=O)OH | |
| 48 | Cl | H | H | S | −CH(CH₂C₆H₅)− | −C(=O)OC₂H₅ | |
| 49 | Cl | H | H | S | −C(C₃H₇(i))(CH₃)− | −C(=O)OH | |
| 50 | Cl | H | H | S | −C(C₃H₇(i))(CH₃)− | −C(=O)NH₂ | |
| 51 | Cl | H | H | S | −C(C₃H₇(i))(CH₃)− | −C(=O)OC₂H₅ | |
| 52 | Cl | H | H | S | −C(C₃H₇(i))(CH₃)− | −CN | |
| 53 | Cl | H | −CH₃ | S | −CH₂− | −C(=O)−pyrrolidin-1-yl | |
| 54 | Cl | H | −CH₃ | S | −CH₂− | −C(=O)−morpholin-4-yl | 150–152 |
| 55 | H | H | −CH₃ | S | −CH₂− | −C(=O)OH | 160–162 |

TABLE 1-continued

Benzoxazol-2-yl- and benzothiazol-2-yl-amino acids and derivatives $$\text{structure with R, R}^1\text{, X, C, R}^2\text{, N-Y-Z}$$

| Example No. | R | R¹ | R² | X | Y | Z | Melting point [°C.] |
|---|---|---|---|---|---|---|---|
| 56 | H | H | —CH₃ | S | —CH₂— | —C(=O)OCH₃ | 91–93 |
| 57 | H | H | —CH₃ | S | —CH₂— | —C(=O)OC₂H₅ | 41–43 |
| 58 | H | H | —CH₃ | S | —CH₂— | —C(=O)O—C₃H₇(i) | 47–49 |
| 59 | H | H | —CH₃ | S | —CH₂— | —C(=O)OCH₂—CH(CH₃)—CH₃ | 56–58 |
| 60 | H | H | —CH₃ | S | —CH₂— | —C(=O)O—C₆H₁₃(n) | 47–49 |
| 61 | H | H | —CH₃ | S | —CH₂— | —C(=O)O—CH₂—CH=CH₂ | 55–57 |
| 62 | H | H | —CH₃ | S | —CH₂— | —C(=O)O—CH₂—C≡CH | 99–103 |
| 63 | H | H | —CH₃ | S | —CH₂—CH₂— | —CN | 90–92 |
| 64 | Cl | H | —CH₃ | S | —CH₂— | —C(=O)NH—C₃H₇(i) | 200–203 |
| 65 | Cl | H | —CH₃ | S | —CH₂— | —C(=O)O—CH₂—CH₂Cl | 95–98 |
| 66 | Cl | H | —CH₃ | S | —CH₂—CH₂— | —CN | 115–117 |
| 67 | Cl | 4-Cl | —CH₃ | S | —CH₂— | —C(=O)OC₂H₅ | 143–144 |
| 68 | Cl | 4-Cl | —CH₃ | S | —CH₂— | —C(=O)O—C₃H₇(i) | 121–122 |

TABLE 1-continued

Benzoxazol-2-yl- and benzothiazol-2-yl-amino acids and derivatives

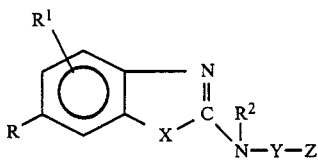

| Example No. | R | R¹ | R² | X | Y | Z | Melting point [°C.] |
|---|---|---|---|---|---|---|---|
| 69 | H | H | —CH₃ | S | —CH₂— | —C(=O)—N(piperidine) | 119–121 |
| 70 | H | H | —CH₃ | S | —CH₂— | —C(=O)—O⁻ Na⁺ | 284–285 (decomposition) |
| 71 | H | H | —CH₃ | S | —CH₂— | —C(=O)—O⁻ H₂N⁺(C₂H₅)₂ | 118–120 |
| 72 | Cl | H | —CH₃ | S | —CH₂— | —C(=O)—O⁻ H₂N⁺(CH₃)(C₄H₉(n)) | 141–143 |
| 73 | Cl | H | —CH₃ | S | —CH₂— | —C(=O)—O⁻ H₃N⁺—C₃H₇(i) | 195–197 |
| 74 | Cl | H | —CH₃ | S | —CH₂—CH₂— | —C(=S)—NH₂ | 184–186 |
| 75 | H | H | H | O | —CH₂— | —COOCH(CH₃)₂ | 115 |
| 76 | Cl | H | —CH₃ | S | —CH₂— | —COOC₈H₁₇(n) | 63–64 |

FORMULATION EXAMPLES

EXAMPLE A

An emulsifiable concentrate is obtained from 15 parts by weight of active substance, 75 parts by weight of cyclohexanone, as a solvent, and 10 parts by weight of oxyethylated nonylphenol (10 EO), as an emulsifier.

EXAMPLE B

A dust is obtained by mixing 10 parts by weight of active substance and 90 parts by weight of talc, as an inert substance, and comminuting the mixture in an impact mill.

EXAMPLE C

A wettable powder which is easily dispersible in water is obtained by mixing 25 parts by weight of active substance, 64 parts by weight of kaolin-containing quartz, as an inert substance, 10 parts by weight of potassium lignin-sulfonate and 1 part by weight of sodium oleylmethyl-tauride, as a wetting and dispersing agent, and grinding the mixture in a pinned disc mill.

BIOLOGICAL EXAMPLES

EXAMPLE 1

Wheat and corn were grown to the 5-leaf stage in a greenhouse and then treated with a herbicide and agents according to the invention with an amount of spray liquor applied at 600 l/ha. The plants were rated for any type of damage 3 weeks after the treatment, the degree of the persistent inhibition of growth being observed in particular.

The results from Table 1 illustrate that the compounds according to the invention can very effectively reduce severe herbicidal damage.

Mixtures of the herbicides and agents according to the invention used are therefore suitable for selectively combating weeds in cereal and corn.

The activity of the various herbicides was not impaired by the addition of the safeners according to the invention; in the application amounts used, of 0.25 or 1.5 kg of active substance, it was always 100%, for example against slender foxtail (*Alopecurus myosuroides*), against wild oat (*Avena fatua*) and against millets, such as species of Echinochloa and Setaria.

The agents according to the invention by themselves cause no damage at all (0% in all cases) to the crop plants at the concentrations used (2.5 kg/ha).

TABLE 1

Antidote action on leaf application with various herbicides (damage to the crop plants in %)

| Compound (Example) | Dose (kg/ha) | Damage to ZM | Damage to TA |
|---|---|---|---|
| H 1 | 0.25 | 80 | — |
| H 2 | 1.5 | — | 80 |
|  | 2.0 | — | 85 |
| H 3 | 0.4 | 95 | — |
| H 1 + 2 | 0.25 + 2.5 | 15 | — |
| H 1 + 26 | 0.25 + 2.5 | 20 | — |
| H 1 + 57 | 0.25 + 2.5 | 25 | — |
| H 2 + 2 | 1.5 + 2.5 | — | 20 |
| H 2 + 9 | 2.0 + 2.5 | — | 40 |
| H 2 + 21 | 2.0 + 2.5 | — | 40 |
| H 2 + 56 | 2.0 + 2.5 | — | 40 |
| H 2 + 57 | 1.5 + 2.5 | — | 10 |
| H 2 + 58 | 2.0 + 2.5 | — | 25 |
| H 2 + 59 | 2.0 + 2.5 | — | 35 |
| H 3 + 3 | 0.4 + 2.5 | 50 | — |
| H 3 + 21 | 0.4 + 2.5 | 35 | — |
| H 3 + 61 | 0.4 + 2.5 | 60 | — |
| H 3 + 62 | 0.4 + 2.5 | 60 | — |

Abbreviations:

ZM = *Zea mays* (corn), TA = *Triticum aestivum* (wheat)

H 1 = methyl 2-[4-(4-bromo-2-chloro-phenoxy)-phenoxy]-propionate (German Patent A-2,601,548)

H 2 = ethyl 2-[4-(6-chloro-benzoxazol-2-yl-oxy)-phenoxy]-propionate; fenoxaprop-ethyl (German Patent A-2,640,730)

H 3 = methyl 2-[4-(2,4-dichlorophenoxy)-phenoxy]-propionate; diclofop-methyl (German Patent A-2,223,894).

We claim:

1. A plant-protecting agent (antidote) of the formula I

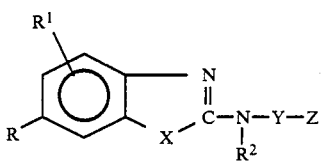

in which X is O or S; R and $R^1$ are hydrogen, or halogen, $R^2$ is $(C_1-C_4)$-alkyl; Y is methylene Z is

$R^3$ is H, $(C_1-C_8)$-alkyl, which can optionally be substituted by halogen or $(C_1-C_2)$-alkoxy, or is $(C_3-C_4)$-alkenyl, $(C_3-C_4)$-alkynyl or an agriculturally acceptable cation.

2. A plant-protecting agent as claimed in claim 1, in which, in a compound of the formula I, X is O or S, R is H, or Cl, $R^1$ is H, $R^2$ is $CH_3$, Y is methylene, and Z is a radical of the formula —$COOR^3$, where $R^3$ is $(C_1-C_8)$-alkyl, $(C_3-C_4)$-alkenyl, $(C_3-C_4)$-alkynyl or an agriculturally acceptable cation.

3. A compound as claimed in claim 1, in which R, $R^1$, $R^2$, $R^3$, $R^4$, $R^5$, X, Y and Z are as there defined, with at least one of the radicals R and $R^1$ being other than hydrogen.

4. A compound as claimed in claim 2, in which R, $R^1$, $R^2$, $R^3$, X, Y and Z are as there defined, with at least one of the radicals R and $R^1$ being other than hydrogen.

5. N-Methyl-N-[6-chloro-benzothiazol-2-yl]-glycine ethyl ester.

6. N-Methyl-N-benzoxazol-2-yl-glycine ethyl ester.

7. N-Methyl-N-benzothiazol-2-yl-glycine ethyl ester.

8. N-Methyl-N-benzothiazol-2-yl-glycine isobutyl ester.

* * * * *